United States Patent [19]
Loree et al.

[11] Patent Number: 5,256,880
[45] Date of Patent: Oct. 26, 1993

[54] PROCESS FOR THE QUALITATIVE ANALYSIS OF PLASTIC PARTICLES

[75] Inventors: Thomas R. Loree, Santa Fe; Robert E. Hermes, Los Alamos, both of N. Mex.

[73] Assignee: Metallgesellschaft Aktiengesellschaft, Frankfurt, Fed. Rep. of Germany

[21] Appl. No.: 825,485

[22] Filed: Jan. 24, 1992

[30] Foreign Application Priority Data

Jan. 31, 1991 [DE] Fed. Rep. of Germany ....... 4102767

[51] Int. Cl.⁵ .......................................... G01N 21/64
[52] U.S. Cl. .............................. 250/461.1; 250/459.1; 356/317
[58] Field of Search ............... 250/461.2, 458.1, 459.1; 356/318, 317; 209/576, 577, 578

[56] References Cited

U.S. PATENT DOCUMENTS 4,105,333 8/1978 Kaule et al. .................... 356/317

FOREIGN PATENT DOCUMENTS 0068086 4/1982 European Pat. Off. .
0293983 5/1988 European Pat. Off. .
0341096 5/1989 European Pat. Off. .
4004627 2/1990 Fed. Rep. of Germany .
0153150 9/1983 Japan .................. 356/317
2234347 6/1990 United Kingdom .

OTHER PUBLICATIONS

Norman S. Allen, "Luminescence applications in commercial polymers," Dec. 2, 1978, pp. 907–913, in *Chemistry and Industry*.

Second International Symposium–Recycling of Metals and Engineered Materials, "Automatic Sorting of Non-Ferrous Metals from Automobile Shredders"; (1990).

Primary Examiner—Paul M. Dzierzynski
Assistant Examiner—Richard Hanig
Attorney, Agent, or Firm—Sprung Horn Kramer & Woods

[57] ABSTRACT

A process and apparatus for the qualitative analysis of particles of various kinds of plastic which comprises passing said particles serially in a predetermined path, irradiating each particle with light of short wavelength from 180 to 500 nm, whereby each particle emits light radiation of a longer wavelength, and detecting such longer wavelength emissions for radiation intensities within a narrow wavelength range to form an emission spectrum, the emission spectrum generating a sorting signal.

13 Claims, 1 Drawing Sheet

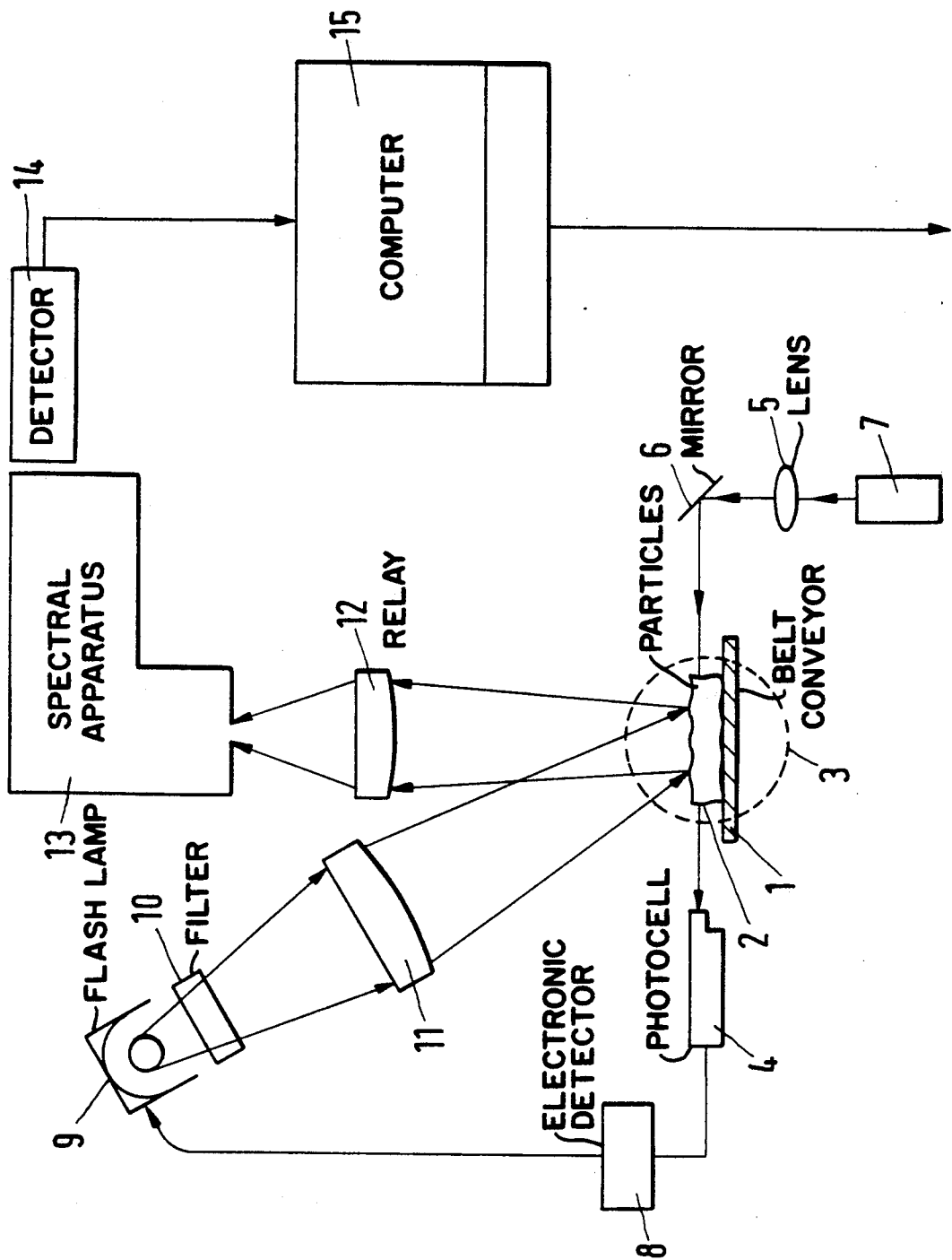

PROCESS FOR THE QUALITATIVE ANALYSIS OF PLASTIC PARTICLES

This invention relates to a process for the qualitative analysis of particles consisting of various kinds of plastic (on the basis of the relative concentration of the predominating kind of plastic) by fluorescence emission spectroanalysis, preferably fluorescence or Raman spectroanalysis, in which the light radiation which is emitted in response to an irradiation of light at shorter wavelengths, preferably UV light, and which has a comparatively long wavelength, is detected for radiation intensities within a relatively narrow wavelength range to form an emission spectrum and predetermined discrete spectral lines (wavelengths) or spectral line ranges (wavelength ranges) of the plastics to be analyzed are detected and utilized for an identification of the plastic particles.

The recycling of used plastics into the economic circulation and the circulation of materials increases in significance because petroleum as the primary raw material and energy are to be saved and the amount of waste is to be decreased. The raw material as well as sufficient space for dumps are available only to a limited extent. Because there are numerous kinds of plastics which differ in their defined mechanical-technological and chemical properties and for this reason are used in different fields, it is not desirable to collect and reuse mixed plastics as the products made therefrom have a comparatively lower value and cannot repeatedly be reused and in part are incompatible with each other. For this reason it is desired to separately collect and reprocess each kind of plastic to be returned to the circulation of material. But that requirement could be met only by a definite and easily legible marking of all products made of plastics. As soon as the design of a product marking has been determined, the moldmakers are called upon to find out how the marking can be incorporated in the molds used to make the plastic products (Heuel, O.: Eindeutige Produktkennzeichnung als Voraussetzung für ein sortenreines Recycling, Kunststoff-Recycling-Tag, Berlin, Sep. 21 and 22, 1989). But this does not preclude a misuse. Because more than 100 plastics are presently in use it is difficult to separately collect them throughout an area and it is necessary to provide separate collecting facilities, which may be supplemented by an organization for collection from the consumers although such systems are undesirable because they involve a high expenditure.

It is known that plastics can be identified by fluorescence spectroscopy, in which the substance to be examined is irradiated with short-wave light, the light which is emitted by the substance and has a longer wavelength is decomposed by suitable spectral apparatus to form an emission spectrum, and the radiation intensity which is characteristic for the substance being examined is detected in dependence on the wavelength and is measured or is converted to proportional electric signals and is evaluated (Allen, N. S. and McKellar, J. F. Chem. and Ind., London 1978, pages 907-913; company publication: Waterloo Scientific Inc. 1989, Photoluminescence Application Note No. 1). But the use of emission spectroanalysis for plastics has previously been substantially restricted to the scientific investigation of plastics.

It is an object of the present invention so to improve the process of emission spectroanalysis which has been described hereinbefore that particles which consist of different kinds of plastic and become available in large quantities can quickly and definitely be identified and can be separated into the several kinds and this can be accomplished in such a manner that the expenditure for the qualitative analysis and for the sorting of the individual plastic particle is distinctly lower than the value which can be added per plastic particle.

That object is accomplished in that each plastic particle is subjected to a pulse of short-wavelength light, a characteristic number is determined in accordance with an algorithm from the radiation intensities of the discrete spectral lines or spectral line ranges, and a sorting signal is generated in response to a comparison of that characteristic number with predetermined limiting values.

In accordance with a preferred feature of the process the plastic particles are irradiated with light having a wavelength from 180 to 500 nm.

According to a further feature of the invention the irradiation light has a triggerable rate from 100 to 600 times per second, preferably 100 to 200 times per second.

According to a preferred feature of the process the plastic particles are arranged to be consecutively spaced apart in a single line and in that arrangement are transported in a continuous flow on a predetermined path from a feeding point through a sensing location, where they are exposed to the short-wavelength light pulses, to a point for a separate delivery of the several kinds.

If the plastic particles are soiled, the surface can be partly cleaned by a pulsed laser beam, the surface dirt being removed in the resulting plasma.

An apparatus is provided which serves to carry out the process which is in accordance with the invention and has been described hereinbefore and that apparatus essentially consists of a light source for generating UV light pulses, a spectral apparatus for generating an emission spectrum, a spectral detector for converting the radiation intensities to electric signals and a computer for processing the electric signals and for generating sorting signals. As the individual plastic particles enter the sensing location they suitably pass through a trigger generator, preferably consisting of an optical barrier, for the generation of a signal by which a UV light pulse is initiated.

To ensure that the output signal of the optical barrier will result in a valid irradiation the individual plastic particles must be spaced at least 1.0 mm apart. A higher speed of transportation will necessitate a larger distance between the individual plastic particles.

The optical barrier consists of a light beam which is directed to a photocell and which can also be used to measure the length of each plastic particle. The light beam is interrupted by the particle to generate the trigger signal.

The optical barrier may alternatively consist of a laser beam or of a combination of a light beam and a laser beam so that each plastic particle may also be three-dimensionally detected.

An apparatus for cleaning the plastic particles by means of a laser may be provided, if desired.

The sensing location is succeeded by a transport path on which the plastic particles are sorted in dependence on their qualitative composition. For instance, sorting may be effected by blowing out the particles as they fall freely through the air.

The light source for generating the UV light pulses may particularly consist of a spectrally filtered pulsed flashlamp, a shuttered and filtered CW flashlamp, an excimer laser, a UV-suppressing CW ion laser, a pulsed solid laser having a frequency multiplier for the UV range, shuttered and filtered fluorescence light, shuttered and filtered sunlight, filtered light from shock waves in noble gases, filtered light from electric discharges, shuttered and filtered light from CW electric arcs, filtered light from laser-induced breakdown sparks, a strobe light, or a photographic flashlamp.

Suitable illuminating optical systems particularly include combinations of transmissive lenses, inclusive of holographic and Fresnel lenses, combinations of convex and concave, spherical and non-spherical reflectors, simple optical fibers with coupling and output optics leading to the above combinations, or optical fiber bundles with coupling and output optics having differently shaped ends connected to the above combinations.

Spectral discriminators employed include grating and prism spectrometers, optical filters of all kinds, interferometers or grating and prism polychromators.

The detectors employed suitably consist of intensified diode arrays, diode arrays, photomultipliers, photodiodes, charge transfer groups (CCD's), groups of pyroelectric elements, video cameras, or spectrally selective light detectors which respond only to predetermined wavelengths.

BRIEF DESCRIPTION OF THE DRAWING

The invention will now be explained in more detail with reference to an example illustrated on the drawing, in which the apparatus is diagrammatically shown.

A belt conveyor 1 for conveying at 3.5 meters per second is used to feed consecutive plastic particles 2 of different kinds of plastic to the sensing location 3. Each plastic particle entering the sensing location 3 blocks photocell 4 from a laser beam, which comes from a He/Ne laser and has been passed through a focusing lens 5 and directed by a mirror 6. The resulting (light) signal is converted by an electronic detector 8 to an electronic signal which is used to initiate the generation of a UV light pulse by the flashlamp 9. The UV light is filtered by the filter 10 and by the illuminating optical system 11 is focussed onto the surface of the plastic particle 2. The radiation emitted by the plastic particle 2 is received via a relay optical system 12 by a spectral apparatus 13, which is succeeded by a detector 14. The electronic signals delivered by the detector 14 are used by the computer 15 to generate relative numerical values, which are compared with predetermined limiting values, whereafter signals for controlling sorting means are derived.

It will be appreciated that the instant specification and claims are set forth by way of illustration and not limitation, and that various modifications and changes may be made without departing from the spirit and scope of the present invention.

What is claimed is:

1. A process for the qualitative analysis of particles of various kinds of plastic which comprises passing said particles serially in a predetermined path, irradiating each particle with light of short wavelength from 180 to 500 nm, whereby each particle emits light radiation, of a longer wavelength, and detecting such longer wavelength emissions for radiation intensities within a narrow wavelength range to form an emission spectrum, the emission spectrum generating a sorting signal.

2. A process according to claim 1, wherein the short wavelength light has a triggerable rate from 100 to 600 times per second.

3. A process according to claim 1, wherein the plastic particles are transported in a continuous flow along a predetermined path from a feeding point through a sensing location where they are exposed to UV light pulses, and then to a point for a separate delivery of the several kinds.

4. A process according to claim 3, wherein the plastic particles are spaced at least 1.0 mm apart.

5. A process according to claim 1, wherein the surfaces of the plastic particles are cleaned by a pulsed laser beam and the resulting plasma is removed.

6. A process according to claim 3, including the further step of separately advancing the several kinds of plastic.

7. An apparatus for the qualitative analysis of particles of various kinds of plastic comprising means for passing said particles serially in a predetermined path to an analyzer and for withdrawing said particles from said analyzer, said analyzer comprising
   a) a light source for generating short-wavelength light pulses,
   b) a spectral apparatus for generating an emission spectrum,
   c) a detector for converting the radiation intensities to electric signals, and
   d) a computer for processing the electric signals for a generation of sorting signals.

8. An apparatus according to claim 7, wherein (a) comprises a signal generator for generating a signal for initiating a UV light pulse.

9. An apparatus according to claim 7, wherein in (a) the signal generator comprises a light beam which is directed to a photocell.

10. An apparatus according to claim 7, wherein the signal generator comprises a laser beam.

11. An apparatus according to claim 7, further including laser means for cleaning the surfaces of the plastic particles.

12. An apparatus according to claim 7, wherein (d) is succeeded by transporting means.

13. An apparatus according to claim 12, wherein the transporting means comprises means for separately advancing the several kinds of plastic identified by the sorting signals.

* * * * *